(12) United States Patent
Kobayashi et al.

(10) Patent No.: US 9,180,278 B2
(45) Date of Patent: Nov. 10, 2015

(54) MEDICAL INSTRUMENT

(75) Inventors: Junichi Kobayashi, Fujinomiya (JP);
Yasushi Kinoshita, Fujinomiya (JP);
Tadashi Kousai, Glasgow (GB)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 313 days.

(21) Appl. No.: 13/058,461

(22) PCT Filed: Aug. 3, 2009

(86) PCT No.: PCT/JP2009/063747
§ 371 (c)(1),
(2), (4) Date: Feb. 10, 2011

(87) PCT Pub. No.: WO2010/018762
PCT Pub. Date: Feb. 18, 2010

(65) Prior Publication Data
US 2011/0152791 A1 Jun. 23, 2011

(30) Foreign Application Priority Data

Aug. 11, 2008 (JP) .................................. 2008-206892

(51) Int. Cl.
*A61M 25/09* (2006.01)
*A61L 29/08* (2006.01)
(Continued)

(52) U.S. Cl.
CPC .............. *A61M 25/09* (2013.01); *A61L 29/085* (2013.01); *A61L 29/14* (2013.01); *A61L 31/10* (2013.01);
(Continued)

(58) Field of Classification Search
CPC ......... A61M 2025/09083; A61M 2025/09091; A61M 2025/09141; A61M 2025/09175; A61M 25/09; A61M 2025/09133

USPC .............. 600/585, 103.1; 604/523–530, 264; 623/1.44
See application file for complete search history.

(56) References Cited

U.S. PATENT DOCUMENTS 3,926,705 A * 12/1975 Todd .............................. 156/155
3,935,139 A * 1/1976 Ashall ........................... 524/594
(Continued)

FOREIGN PATENT DOCUMENTS

EP 2 140 904 A1 1/2010
JP 9-501593 A 2/1997
(Continued)

OTHER PUBLICATIONS

Supplementary European Search Report dated Dec. 29, 2011, issued by the European Patent Office in the corresponding European Application No. 09806655.8. (6 pages).
(Continued)

*Primary Examiner* — Aarti B Berdichevsky
*Assistant Examiner* — Matthew A Engel
(74) *Attorney, Agent, or Firm* — Buchanan Ingersoll & Rooney PC

(57) ABSTRACT

A medical instrument to be inserted into a living body before being used. The medical instrument is provided with a medical instrument main body including a long linear body having flexibility on which a coating layer covering at least the outer periphery on the distal side thereof is formed. The coating layer composes of a first layer which includes a material containing a low-friction resin material capable of lowering friction and a binder resin material serving as a binder; a second layer which is formed on the first layer and includes a material containing a low-friction resin material and a pigment and in which the content of a binder resin material is lower than the binder resin material content of the first layer or nil; and a third layer which is formed on the second layer and includes a material containing a low-friction resin material.

15 Claims, 8 Drawing Sheets

(51) Int. Cl.
  *A61L 29/14* (2006.01)
  *A61L 31/10* (2006.01)
  *A61L 31/14* (2006.01)
  *A61M 25/00* (2006.01)

(52) U.S. Cl.
  CPC ............ *A61L 31/14* (2013.01); *A61M 25/0045* (2013.01); *A61L 2420/08* (2013.01); *A61M 2025/0008* (2013.01); *A61M 2025/09083* (2013.01); *A61M 2025/09091* (2013.01); *A61M 2025/09108* (2013.01); *A61M 2025/09166* (2013.01)

(56) References Cited

U.S. PATENT DOCUMENTS

| | | | | |
|---|---|---|---|---|
| 3,980,453 | A * | 9/1976 | Fukuda | 51/297 |
| 4,985,019 | A * | 1/1991 | Michelson | 604/180 |
| 5,084,022 | A * | 1/1992 | Claude | 604/164.13 |
| 5,163,921 | A * | 11/1992 | Feiring | 604/247 |
| 5,213,111 | A * | 5/1993 | Cook et al. | 600/585 |
| 5,228,453 | A * | 7/1993 | Sepetka | 600/585 |
| 5,272,012 | A * | 12/1993 | Opolski | 428/423.1 |
| 5,304,205 | A * | 4/1994 | Shinoda et al. | 606/230 |
| 5,344,419 | A * | 9/1994 | Spears | 606/15 |
| 5,358,493 | A * | 10/1994 | Schweich et al. | 604/264 |
| 5,379,779 | A * | 1/1995 | Rowland et al. | 600/585 |
| 5,404,887 | A * | 4/1995 | Prather | 600/585 |
| 5,432,000 | A * | 7/1995 | Young et al. | 428/372 |
| 5,443,907 | A * | 8/1995 | Slaikeu et al. | 428/375 |
| 5,507,995 | A * | 4/1996 | Schweich et al. | 264/293 |
| 5,545,151 | A * | 8/1996 | O'Connor et al. | 604/524 |
| 5,646,076 | A * | 7/1997 | Bortz | 442/136 |
| 5,746,717 | A * | 5/1998 | Aigner | 604/102.03 |
| 5,756,144 | A * | 5/1998 | Wolff et al. | 427/2.3 |
| 5,820,607 | A * | 10/1998 | Tcholakian et al. | 604/265 |
| 5,824,049 | A * | 10/1998 | Ragheb et al. | 623/1.44 |
| 5,827,201 | A * | 10/1998 | Samson et al. | 600/585 |
| 5,908,406 | A * | 6/1999 | Ostapchenko et al. | 604/96.01 |
| 5,965,276 | A * | 10/1999 | Shlenker et al. | 428/492 |
| 5,998,085 | A * | 12/1999 | Isberg et al. | 430/200 |
| 6,027,848 | A * | 2/2000 | Pai et al. | 430/119.72 |
| 6,083,167 | A * | 7/2000 | Fox et al. | 600/439 |
| 6,086,547 | A * | 7/2000 | Hanssen et al. | 600/585 |
| 6,203,505 | B1 * | 3/2001 | Jalisi et al. | 600/585 |
| 6,361,557 | B1 * | 3/2002 | Gittings et al. | 623/1.13 |
| 6,485,735 | B1 * | 11/2002 | Steen et al. | 424/423 |
| 6,591,472 | B1 * | 7/2003 | Noone et al. | 29/417 |
| 6,593,255 | B1 * | 7/2003 | Lawton et al. | 442/59 |
| 6,652,507 | B2 * | 11/2003 | Pepin | 604/523 |
| 6,689,120 | B1 * | 2/2004 | Gerdts | 604/526 |
| 6,702,782 | B2 * | 3/2004 | Miller et al. | 604/96.01 |
| 6,786,876 | B2 * | 9/2004 | Cox | 600/585 |
| 6,811,875 | B2 * | 11/2004 | Kikuchi et al. | 428/372 |
| 6,811,958 | B2 * | 11/2004 | Iwami et al. | 430/320 |
| 6,817,995 | B1 * | 11/2004 | Halpern | 604/524 |
| 6,945,970 | B2 * | 9/2005 | Pepin | 604/525 |
| 7,081,096 | B2 * | 7/2006 | Brister et al. | 600/549 |
| 7,175,607 | B2 * | 2/2007 | Lim et al. | 604/103.06 |
| 7,335,184 | B2 * | 2/2008 | Laguna | 604/101.02 |
| 7,651,469 | B2 * | 1/2010 | Osborne et al. | 600/585 |
| 7,687,144 | B2 * | 3/2010 | Clark et al. | 428/383 |
| 7,766,049 | B2 * | 8/2010 | Miller et al. | 138/116 |
| 7,942,581 | B2 * | 5/2011 | Leonardelli | 384/276 |
| 8,034,045 | B1 * | 10/2011 | Lyons | 604/526 |
| 8,106,474 | B2 * | 1/2012 | Yamazaki et al. | 257/459 |
| 8,187,206 | B2 * | 5/2012 | Kinoshita et al. | 600/585 |
| 8,197,424 | B2 * | 6/2012 | Nabeshima | 600/585 |
| 8,231,647 | B2 * | 7/2012 | Eidenschink | 606/194 |
| 8,317,772 | B2 * | 11/2012 | Jansen et al. | 604/527 |
| 8,353,868 | B2 * | 1/2013 | Davies et al. | 604/103.06 |
| 8,795,255 | B2 * | 8/2014 | Jansen et al. | 604/527 |
| 9,028,427 | B2 * | 5/2015 | Kinoshita et al. | 600/585 |
| 2004/0098021 | A1 * | 5/2004 | Laguna | 606/194 |
| 2008/0078946 | A1 | 4/2008 | Yamada et al. | |
| 2010/0298812 | A1 * | 11/2010 | Wolkenstorfer | 604/523 |

FOREIGN PATENT DOCUMENTS

| | | |
|---|---|---|
| JP | 2001-046508 | 2/2001 |
| JP | 2003-250905 A | 9/2003 |
| JP | 3587567 B2 | 11/2004 |
| JP | 2006-068497 | 3/2006 |
| JP | 2008-086575 A | 4/2008 |
| WO | WO 2008/046636 A2 * | 4/2008 |

OTHER PUBLICATIONS

International Search Report (PCT/ISA/210) issued on Oct. 20, 2009, by Japanese Patent Office as the International Searching Authority for International Application No. PCT/JP2009/063747.

* cited by examiner

MEDICAL INSTRUMENT

TECHNICAL FIELD

The present invention relates to a medical instrument to be inserted into a living body when being used, such as a guide wire or a catheter.

BACKGROUND ART

In observation or treatment of a body lumen or the like by use of an endoscope, a guide wire is used for guiding the endoscope or a catheter inserted in the lumen of the endoscope to a predetermined position in the body lumen or the like.

In inserting the guide wire, a movement of the guide wire in the axial direction cannot be sensed if the guide wire is monochromatic; therefore, it is preferable that a marker indicative of position or the like is provided on the surface of the guide wire. In view of this, methods for providing guide wires with various marks have hitherto been proposed.

For example, a method has been known in which a hollow tube formed of polytetrafluoroethylene or the like and having a plurality of colored stripes is adhered to a distal portion of a core member of a guide wire by putting the hollow tube over the distal portion in an enveloping manner through heat shrinkage (see, for example, Patent Document 1).

Since there is a limit to the shrinkage of the hollow tube, however, it is impossible by this method to render the wall portion of the tube sufficiently thin, even by application of heat shrinkage to the tube. Therefore, flexibility of the distal portion of the guide wire is not secured sufficiently, so that the distal portion would be too hard to be inserted into a living body. Besides, in this method, adhesion of the hollow tube onto the core member is performed through the steps of inserting the core member into the hollow tube and, further, heating the hollow tube in this condition. Consequently, the guide wire manufacturing process would be complicated, and the manufacturing cost would be increased.

Besides, in the guide wire described in Patent Document 1, by preparing the hollow tube which has a light color and adhering the hollow tube onto the core member, it is possible to ensure that the marker composed of the hollow tube has an enhanced contrast. However, the guide wire described in Patent Document 1 is poor in flexibility, as above-mentioned.

In view of this problem, in Patent Document 1, not only the configuration in which the marker is composed of the hollow tube as above-mentioned is described, but also a method is mentioned in which a member obtained by applying a coating material to a distal portion of the core member and drying the coating material is made to function as a marker. In this case, it may be possible to secure flexibility of the distal portion of the guide wire as much as possible, but the marker would be discolored into a color difficult to visually confirm (for example, a blackish deep blue). The reason for discoloration into such a color may be as follows.

As the coating material to be applied, there may be contemplated one which contains a low-friction material, a pigment and a binder resin material, and in which, particularly, the binder resin material among these constituent materials is contained in a large amount. In this case, during drying of the coating material, the binder resin material may be discolored, for example, to yellow or liver brown or the like color by the heat for drying. As a result, the marker obtained would have a mixed color of the color of the discolored binder resin material and the color of the pigment, in other words, would appear to have been discolored into a color difficult to visually confirm.

Patent Document 1: Japanese Unexamined Patent Application Publication No. Hei 9-501593

DISCLOSURE OF INVENTION

It is an object of the present invention to provide a medical instrument in which flexibility of a portion on the distal side can be secured assuredly and the position of the portion in a living body can be grasped easily and assuredly.

In order to attain the above object, according to the present invention, there is provided a medical instrument to be inserted into a living body when being used, including:

a medical instrument main body which includes a long linear body having flexibility and on which a coating layer covering at least the outer periphery on the distal side thereof is formed, wherein the coating layer includes:

a first layer which includes a material containing a low-friction resin material capable of reducing friction and a binder resin material functioning as a binder;

a second layer which is formed on the first layer and includes a material containing the low-friction resin material and a pigment and in which the content of the binder resin material is lower than the binder resin material content of the first layer or nil; and a third layer which is formed on the second layer and includes a material containing the low-friction resin material.

This ensures that, since the first layer serves as a ground for the second layer at least at a portion on the distal side of the medical instrument, the second layer will be comparatively high in brightness and saturation. As a result, the coating layer, particularly, the second layer can be clearly confirmed visually, so that the position of the distal-side portion of the medical instrument in a living body can be grasped easily and securely.

In addition, the thicknesses of the layers constituting the coating layer can respectively be set appropriately. This ensures that the coating layer can be prevented from becoming excessively thick, so that flexibility of the distal-side portion of the medical instrument can be secured in an assured manner.

Besides, in the medical instrument of the present invention, preferably, the coating layer has a function of indicating the position of the medical instrument main body in a living body.

This ensures that the second layer is comparatively high in brightness and saturation. Therefore, for example in the case of observing the medical instrument from outside a living body through an endoscope, the second layer can be clearly checked visually. Consequently, the position of the distal-side portion (the portion protruding from the distal end of the lumen of an endoscope or a catheter) of the medical instrument in a living body can be grasped easily and assuredly.

In addition, in the medical instrument of the present invention, preferably, the first layer is the smallest in average thickness, among the first layer, the second layer and the third layer.

This enables the overall thickness of the coating layer to be small to such an extent that the second layer can be clearly confirmed visually. Besides, according to the reduction in the thickness of the coating layer as a whole, flexibility of the medical instrument can be secured assuredly. In addition, there is a merit that the reduction in diameter promises a lowering in sliding resistance.

Besides, in the medical instrument of the present invention, preferably, the average thickness of the second layer is equal to or greater than the average thickness of the third layer.

This ensures that the second layer is particularly emphasized in the coating layer, so that the second layer can be visually confirmed more clearly.

In addition, in the medical instrument of the present invention, preferably, the second layer contains the binder resin material, and the content of the binder resin material is less than 0.5 times the binder resin material content of the first layer.

This ensures that, at the time of drying a liquid material formed upon liquidizing of the material constituting the second layer during formation of the second layer, the binder resin material is securely restrained from being discolored, for example, to yellow or liver brown or the like color by the heat for drying. Consequently, the color of the second layer itself will be one in which the color of the pigment in the second layer appears with priority, that is, will be mainly the color of the pigment in the second layer. Accordingly, the second layer will be clearly confirmed visually.

Besides, in the medical instrument of the present invention, preferably, the low-friction resin material is a fluoro-resin material.

This ensures that, in the case where the medical instrument is inserted for example into the lumen of an endoscope when put to use, the frictional resistance (sliding resistance) between an inner wall defining the lumen and the medical instrument is reduced, whereby slidability is enhanced, and operability of the medical instrument in the lumen of the endoscope is more enhanced. In addition, the lowering in the sliding resistance of the medical instrument makes it possible to more securely prevent the medical instrument from kinking (sharp bending) or twisting at the time when the medical instrument is moved and/or rotated inside the endoscope.

Besides, in the medical instrument of the present invention, preferably, the pigment is an inorganic pigment.

This ensures that the layer containing the inorganic pigment has resistance to heat.

In addition, in the medical instrument of the present invention, preferably, the first layer contains a pigment different in color from the pigment in the second layer.

This ensures that the second layer is comparatively high in brightness and saturation. Therefore, in the case where the medical instrument is observed for example through an endoscope, the second layer can be clearly confirmed visually. Consequently, the position of a distal-side portion (a portion protruding from the distal end of the lumen of the endoscope or a catheter) of the medical instrument in a living body can be grasped easily and assuredly.

Besides, in the medical instrument of the present invention, preferably, the color of the pigment in the first layer is deeper than the color of the pigment in the second layer.

This ensures that the second layer is comparatively high in brightness and saturation, so that the second layer can be clearly confirmed visually in the case of observing the medical instrument from outside a living body through an endoscope, for example. Consequently, the position of a distal-side portion (a portion protruding from the distal end of the lumen of an endoscope or a catheter) of the medical instrument in a living body can be grasped easily and assuredly.

In addition, in the medical instrument of the present invention, preferably, a marker which has a function of indicating the position of the medical instrument main body in a living body and includes a material containing a pigment different in color from the pigment in the second layer is disposed between the second layer and the third layer.

This ensures that the position of a distal-side portion of the medical instrument in a living body can be grasped more easily and securely.

Besides, in the medical instrument of the present invention, preferably, the marker is wound spirally.

This ensures that the position of a distal-side portion of the medical instrument in a living body can be grasped more easily and assuredly.

In addition, in the medical instrument of the present invention, preferably, the marker has a first linear portion and a second linear portion made to intersect each other at a plurality of positions so that the marker as a whole is grid-like in shape.

This ensures that when the medical instrument is moved along its axis or rotated about the axis, the fashion in which the marker is seen is changed, whereby whether the actual displacement of the medical instrument is movement or rotation can be discriminated assuredly.

Besides, in the medical instrument of the present invention, preferably, the marker has the first linear portion and the second linear portion raised in radial direction of the medical instrument main body; and at intersection portions where the first linear portion and the second linear portion intersect each other, one of the first linear portion and the second linear portion is laid on the other.

This ensures that, in the case where the medical instrument is inserted for example into the lumen of an endoscope when put to use, coating of the second coating layer with a third coating layer results in that the intersection portions of the first linear portion and the second linear portion raise the third coating layer. Therefore, the area of contact between the outer surface of the third layer and the inner wall defining the lumen of the endoscope is reduced, whereby frictional resistance (sliding resistance) is reduced, slidability is enhanced, and operability of the medical instrument is improved.

In addition, in the medical instrument of the present invention, preferably, the third layer has a raised portion which is raised from an outer surface thereof.

This ensures that, in the case where the medical instrument is inserted for example into the lumen of an endoscope when put to use, coating of the second coating layer with a third coating layer results in that the intersection portions of the first linear portion and the second linear portion raise the third coating layer. Therefore, the area of contact between the outer surface of the third layer and the inner wall defining the lumen of the endoscope is reduced, whereby frictional resistance (sliding resistance) is reduce, slidability is enhanced, and operability of the medical instrument is improved.

Besides, in the medical instrument of the present invention, the medical instrument is a guide wire, a catheter or a dilator.

This ensures that flexibility of a distal-side portion of the medical instrument is secured assuredly, and the position of the portion in a living body can be grasped easily and assuredly.

BEST MODE FOR CARRYING OUT THE INVENTION

Now, the medical instrument according to the present invention will be described in detail below, based on preferred embodiments shown in the accompanying drawings.

<First Embodiment>

Figure 1:
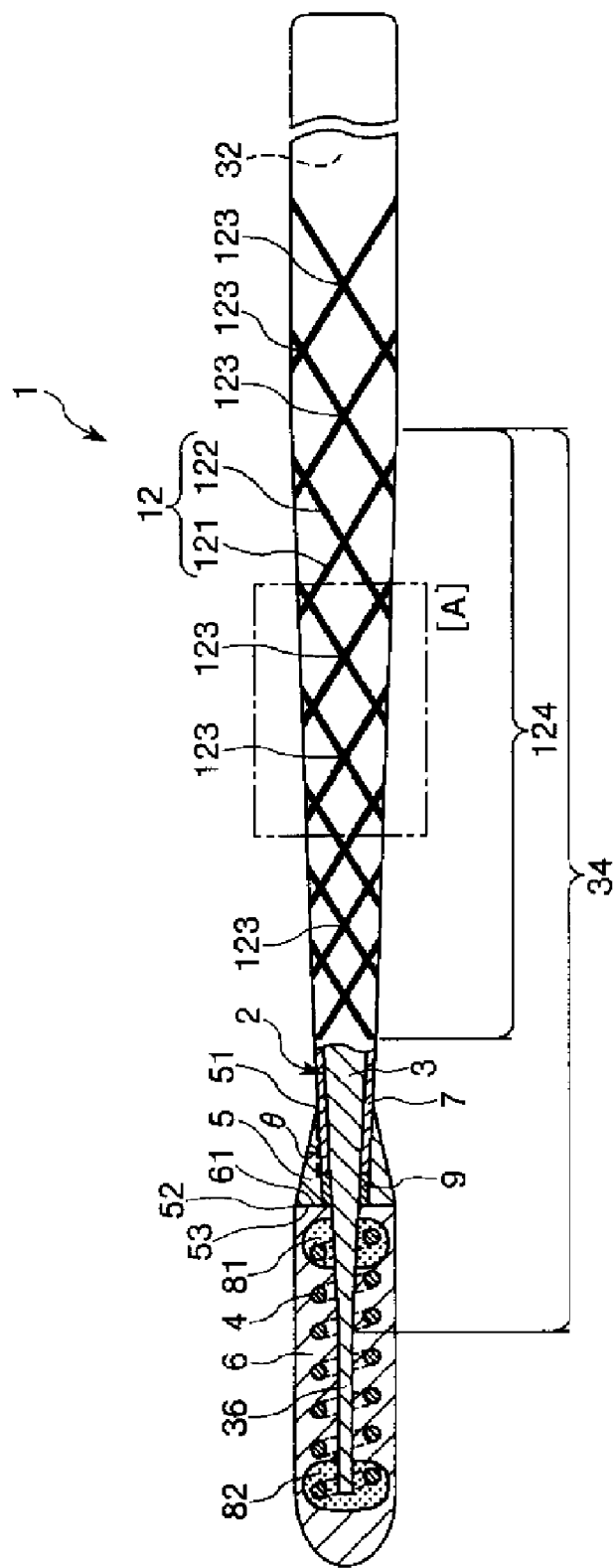
FIG. 1 is a partial longitudinal sectional view showing an embodiment (first embodiment) in the case where the medical instrument of the present invention is applied to a guide wire.
Figure 2:
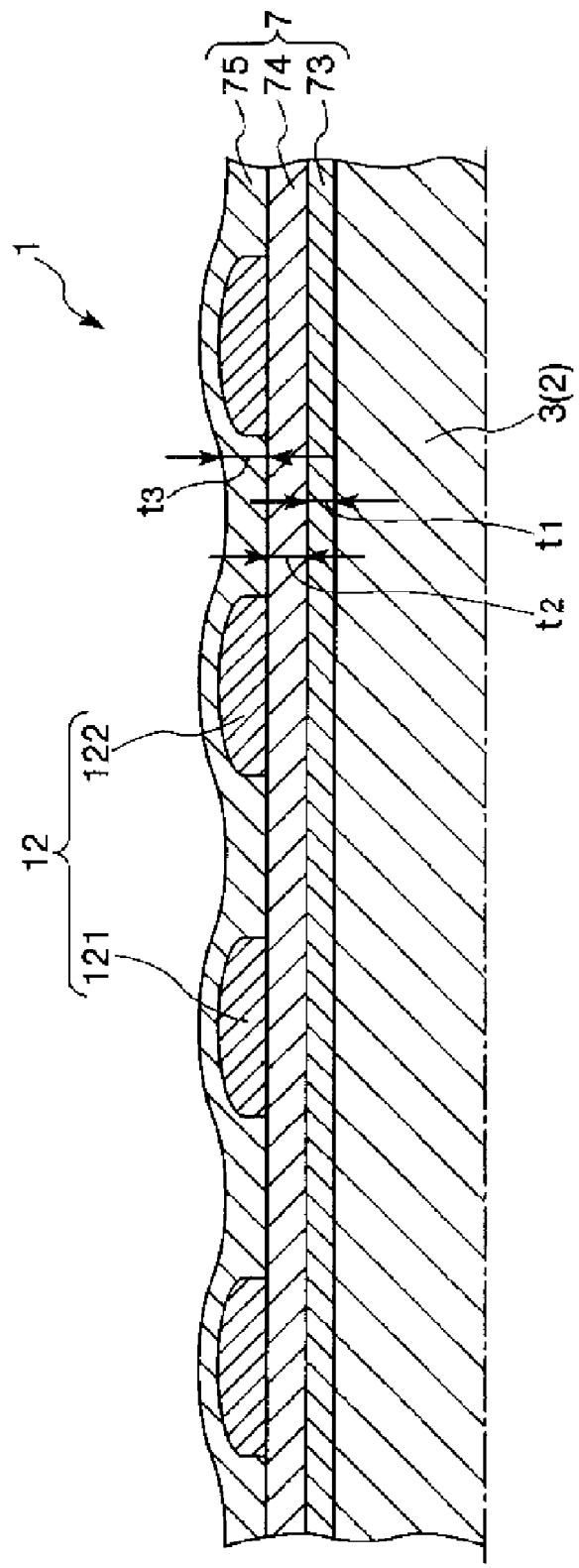
FIG. 2 is an enlarged longitudinal sectional view of region [A] surrounded by dot-dash line in FIG. 1.
Figure 3:
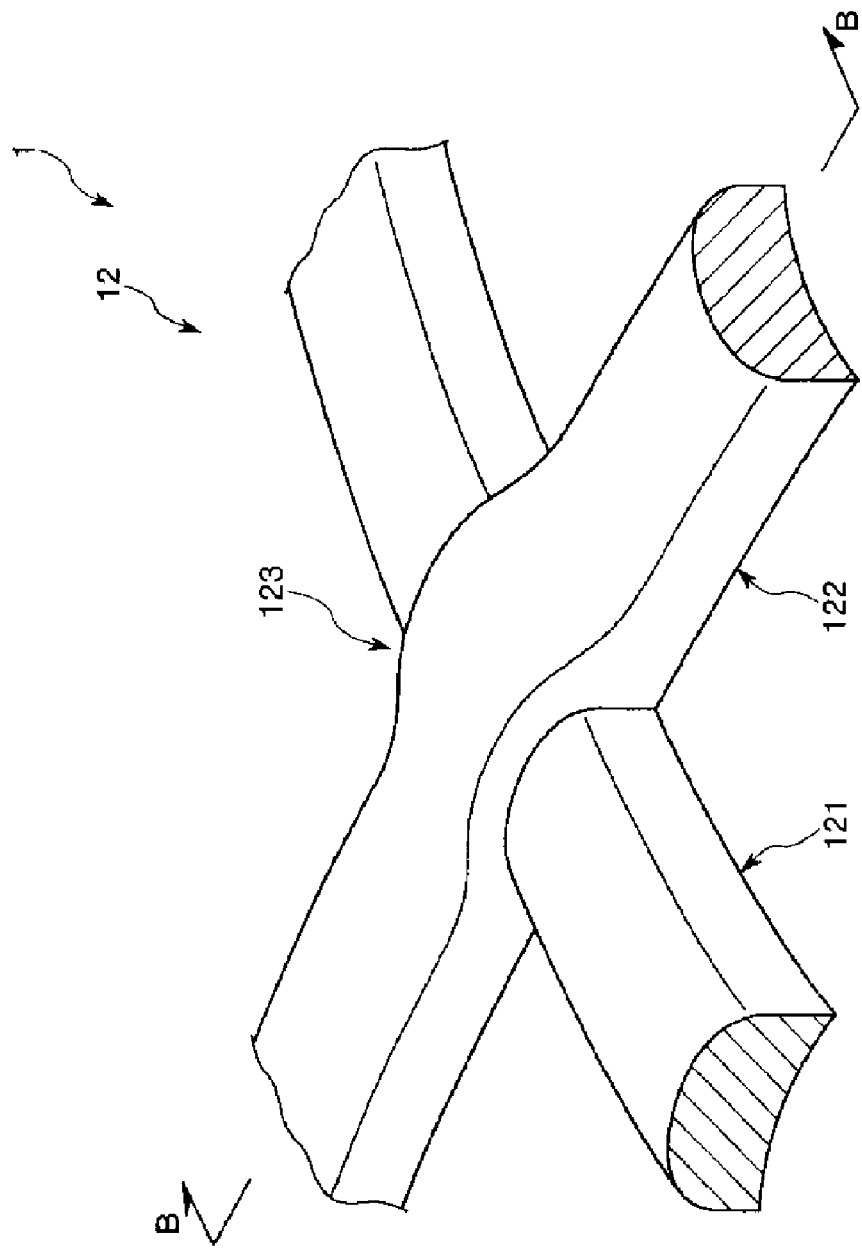
FIG. 3 is a perspective view of a marker in the guide wire shown in FIG. 1.
Figure 4:
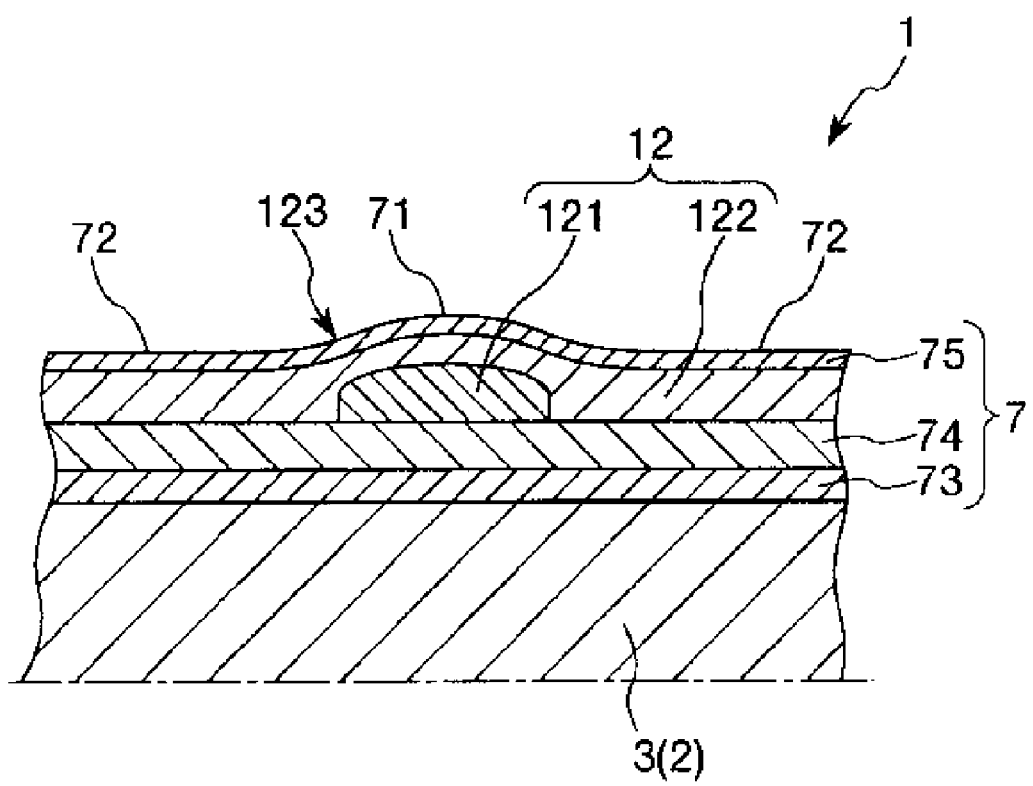
FIG. 4 is a sectional view taken along line B-B of FIG. 3.
Figure 5:
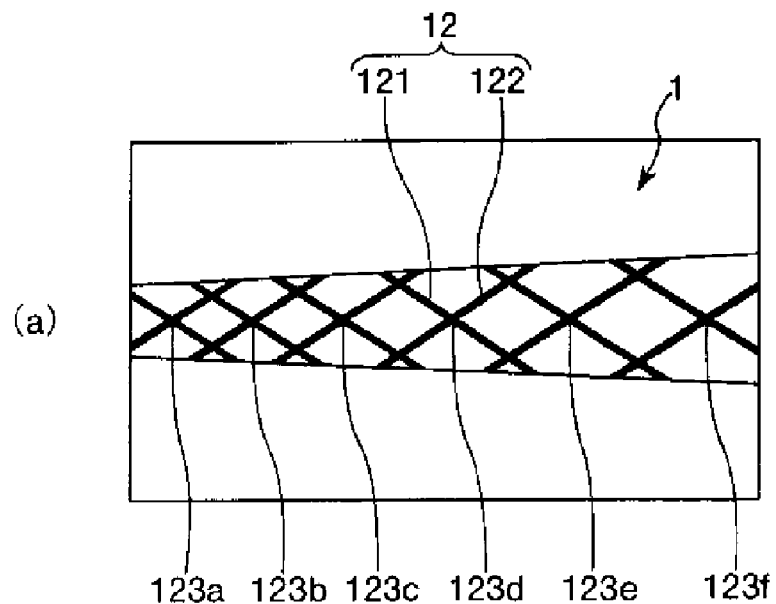
FIG. 5 illustrates the process of a change in the marker when the guide wire shown in FIG. 1 is rotated about its axis.
Figure 5:
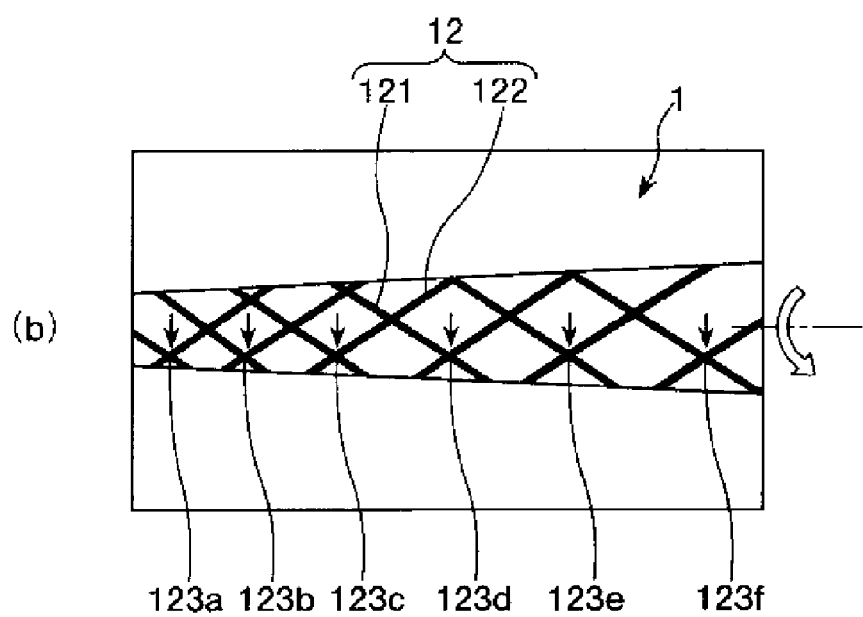
Figure 6:
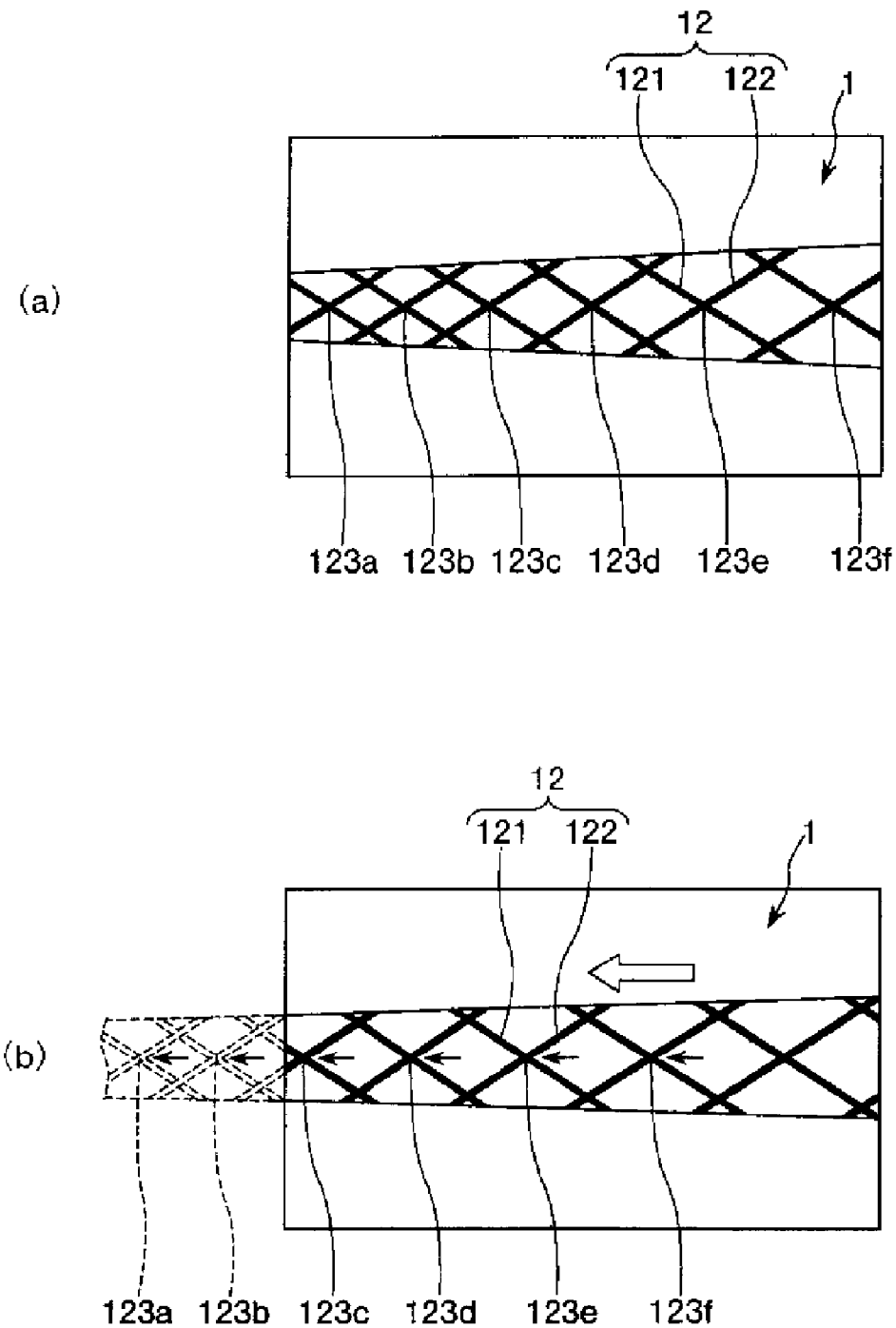
FIG. 6 illustrates the process of a change in the marker when the guide wire shown in FIG. 1 is moved along the axial direction thereof.

FIG. 1 is a partial longitudinal sectional view showing an embodiment (first embodiment) in the case where the medical instrument of the present invention is applied to a guide wire; FIG. 2 is an enlarged longitudinal sectional view of region [A] surrounded by dot-dash line in FIG. 1; FIG. 3 is a perspective view of a marker in the guide wire shown in FIG. 1; FIG. 4 is a sectional view taken along line B-B of FIG. 3; FIG. 5 illustrates the process of a change in the marker when the guide wire shown in FIG. 1 is rotated about its axis; and FIG. 6 illustrates the process of a change in the marker when the guide wire shown in FIG. 1 is moved along the axial direction thereof. Incidentally, in the following, for convenience of description, the right side in FIGS. 1, 2, 5 and 6 (and in FIGS. 7 and 8, as well) will be referred to as "proximal (side)," and the left side as "distal (side)." Besides, in FIG. 1, for easy understanding, the guide wire is schematically shown in the state of being contracted in the lengthwise direction and being exaggerated in the radial direction, and, therefore, the ratio of length to radial size is different from the actual ratio.

The guide wire 1 shown in FIG. 1 is a catheter guide wire to be used in the state of being inserted a lumen of a catheter or an endoscope. The guide wire 1 includes a wire main body (medical instrument main body) 2 composed of a linear body having flexibility, a spiral coil 4, a resin coating layer 6, an annular member 5, and a marker 12. The whole length of the guide wire 1 is preferably, for example, about 200 to 5000 mm.

As shown in FIG. 1, the wire main body 2 has a single long (linear), continuous core wire (core member) 3, and a coating layer 7 with which the outer periphery of the core wire 3 is coated.

The core wire 3 is circular in cross-sectional shape. It should be noted, however, that this is not limitative of the present invention, and the core wire 3 may be one in which a plurality of core wires (wire members) of the same or different materials are joined (connected) to each other by, for example, welding, soldering (brazing) or the like. Incidentally, in the case where the core wire 3 is for example obtained by joining two core wires, the joint portion may be located at any one of a main body portion 32, a tapered portion 34, and a small-diameter portion 36, which will be described later.

The core wire 3 extends over substantially the whole length of the guide wire 1, and includes the main body portion 32 corresponding to the main body part of the guide wire 1, the tapered portion (gradually decreasing outside diameter portion) 34 located on the distal side thereof, and the small-diameter portion 36 located on the distal side thereof. The main body portion 32 is substantially constant in outside diameter, whereas the tapered portion 34 gradually decreases in outside diameter along the distal direction (is tapered), and the small-diameter portion 36 is substantially constant in outside diameter.

Since the core wire 3 is provided with the tapered portion 34, flexibility of the core wire 3 gradually (continuously) increases in the distal direction from the vicinity of a boundary portion between the main body portion 32 and the tapered portion 34. As a result, flexibility of the guide wire 1 is increased, so that operability and safety at the time of insertion into a living body are enhanced.

A marker 12 is formed in the range from an intermediate portion of the tapered portion 34 toward the proximal side (see FIG. 1). As a result, the marker 12 is arranged at that portion at which flexibility is comparatively high, namely, that portion which is easily deformable, of the guide wire 1 (wire main body 1). Accordingly, when the portion is curved (deformed), the extent of the curving can be confirmed assuredly.

In addition, with the small-diameter portion 36 provided on the distal side of the tapered portion 34, the flexible portion at the most distal side can be made long, which produces an effect of rendering the most distal portion more flexible.

Besides, at least a part of the small-diameter portion 36 of the core wire 3 may be a reshapable portion capable of being reshaped. The reshapable portion is preferably in the shape of a flat plate, a prism or the like.

The outside diameter of the main body portion 32 of the core wire 3 is, for example, preferably about 0.3 to 1.0 mm, more preferably about 0.4 to 0.7 mm.

The outside diameter of the small-diameter portion 36 of the core wire 3 is, for example, preferably about 0.05 to 0.3 mm, more preferably about 0.1 to 0.2 mm. Incidentally, the small-diameter portion 36 being constant in outside diameter is not limitative, and its outside diameter may gradually decreases toward the distal end.

In addition, the length of the tapered portion 34 varies depending on the use and/or kind of the guide wire 1, and may be preferably about 10 to 300 mm, more preferably about 30 to 250 mm.

Besides, the length of the small-diameter portion 36 may be preferably about 0 to 100 mm, more preferably about 10 to 50 mm.

Incidentally, the taper angle (the rate of reduction in outside diameter) of the tapered portion 34 may be constant along the longitudinal direction of the core wire 3 (wire main body 2); or, alternatively, there may be some part(s) where the taper angle varies along the longitudinal direction. In addition, the tapered portion 34 is not limited to one portion, but two or more such tapered portions may be provided.

Examples of the material constituting the core wire 3 include various metallic materials such as stainless steel, superelastic alloys such as Ni—Ti alloys, Ni—Al alloys, Cu—Zn alloys, etc., and resin materials having comparatively high rigidity, which may be used either singly or in combination of two or more of them.

Besides, a coil 4 is disposed on the outer periphery of a distal portion of the core wire 3 (wire main body 2), that is, in the configuration shown, on the outer periphery of the small-diameter portion 36 of the core wire 3 and on the outer periphery of a portion ranging to an intermediate portion of the tapered portion 34 of the core wire 3. The coil 4 is a member formed by spirally winding a filament (thin wire), and is so disposed as to cover the outer periphery of a distal portion of the core wire 3 (wire main body 2). In the configuration shown, the distal portion of the core wire 3 is passed through a substantially central part of the inside of the coil 4.

In addition, the distal portion of the core wire 3 is passed in the state of not making contact with the inner surface of the coil 4.

The proximal end of the coil 4 is located at an intermediate portion of the tapered portion 34 of the core wire 3, and the marker 12 is located on the proximal side thereof. This ensures that the coil 4 and the marker 12 can be prevented from positionally interfering with each other, so that the guide wire 1 is simplified in structure. Incidentally, the marker 12 may be so formed as to range to the side of the outer periphery of the coil 4, that is, so formed as to overlap with the coil 4 in side view.

Incidentally, in the configuration shown, the coil 4 has gaps left between turns of the spirally wound filament in the condition where no external force is exerted thereon. However, a configuration may be adopted in which, unlike the configuration shown, turns of the spirally wound filament are closely disposed without any gap therebetween in the condition where no external force is exerted thereon.

The coil 4 is preferably formed of a metallic material. Examples of the metallic material constituting the coil 4 include stainless steel, superelastic alloys, cobalt alloys, noble metals such as gold, platinum, tungsten, etc. and alloys containing them (for example, platinum-iridium alloys). Especially, in the case where the coil 4 is formed of a radiopaque material (material having radiopacity) such as noble metals, the guide wire 1 can have radiopacity and can be inserted into a living body while checking the position of its distal portion under radioscopy. In addition, the coil 4 may be formed of different materials on the distal side and on the proximal side, respectively. For example, a configuration may be adopted in which the coil 4 is composed of a coil of a radiopaque material on the distal side thereof and composed of a coil of a material comparatively transparent to X-rays (such as stainless steel) on the proximal side thereof. Incidentally, the overall length of the coil 4 is preferably about 5 to 500 mm. In addition, while the coil 4 is formed by use of a filament which is circular in cross section in the present embodiment, this is not limitative; for example, the cross-sectional shape of the filament may be an ellipse, a tetragon (particularly, a rectangle) or the like.

A proximal portion and a distal portion of the coil 4 are fixed (attached) to the core wire 3 by fixing materials 81 and 82, respectively.

The fixing materials 81 and 82, or two fixing portions for fixing the core wire 3 and the coil 4 to each other, are provided on the distal side relative to the annular member 5 to be described later, and are not in contact with the annular member 5. This ensures that conduction between the core wire 3 and the annular member 5 through the fixing material 81 can be prevented, and, accordingly, conduction between the outer surface of the guide wire and the core wire 3 can be prevented.

The fixing materials 81 and 82 are each formed of solder (brazing material). Incidentally, the fixing materials 81 and 82 are not limited to solder; for example, they may each be an adhesive. In addition, the method of fixing the coil 4 is not limited to the method relying on the fixing materials; for example, the fixation may be achieved by welding.

Besides, the guide wire 1 has a resin coating layer 6 which covers the outer surfaces of a distal portion of the core wire 3 (wire main body 2), the coil 4, and the fixing materials 81 and 82. The resin coating layer 6 is in secure contact with the outer surface of the distal portion of the core wire 3.

Incidentally, while the resin coating layer 6 is entering into the inside of the coil 4 in the configuration shown, it may not necessarily enter into the inside of the coil 4.

The resin coating layer 6 can be formed for various purposes, one example of which is for enhancing the safety in inserting the guide wire 1 into a blood vessel or the like. For this purpose, the resin coating layer 6 is preferably formed of a material rich in flexibility (flexible material, or elastic material). Examples of the material include polyolefins such as polyethylene, polypropylene, etc., polyvinyl chloride, polyesters (PET, PBT, etc.), polyamides, polyimides, polyurethane, polystyrene, silicone resin, thermoplastic elastomers such as polyurethane elastomer, polyester elastomer, polyamide elastomer, etc., various rubber materials such as latex rubber, silicone rubber, etc., and composite materials obtained by combining two or more of these materials.

Especially, in the case where the resin coating layer 6 is formed of one of the above-mentioned thermoplastic elastomers and various rubber materials, a distal portion of the guide wire 1 is more enhanced in flexibility. Therefore, at the time of insertion into a blood vessel or the like, damaging of blood vessel inside wall or the like can be more securely prevented from occurring, and, hence, extremely high safety is secured.

In addition, particles (filler) composed of a radiopaque material (material having radiopacity) may be dispersed in the resin coating material 6. This ensures that the guide wire 1 can have radiopacity, and can be inserted into a living body while checking the position of a distal portion thereof under radioscopy. Examples of the material constituting the particles include noble metals such as gold, platinum, tungsten, etc. and alloys containing them (e.g., platinum-iridium alloy).

The thickness of the resin coating layer 6 is appropriately set taking into account the purpose of formation, the constituting material, the forming method and the like of the resin coating layer 6. Normally, the average thickness of the resin coating layer 6 is preferably about 30 to 300 μm, more preferably 50 to 200 μm. Incidentally, the "average thickness" is a thickness determined by selecting five arbitrary points in the area where the object layer is present, and obtaining the average of thickness values at the five points. The "average thickness" described below has the same meaning. If the resin coating layer 6 is too thin, the purpose of formation of the resin coating layer 6 may fail to be fulfilled. If the resin coating layer 6 is too thick, on the other hand, it may have influences on physical properties of the wire main body 2 (guide wire 1). Incidentally, the resin coating layer 6 may be a laminate of two or more layers.

In addition, a distal end surface of the resin coating layer 6 is rounded. This ensures that, at the time of inserting the guide wire 1 into a blood vessel or the like, the distal end surface of the resin coating layer 6 (guide wire 1) can be more securely prevented from damaging the blood vessel inside wall or the like.

The guide wire 1 has, on the proximal side of the resin coating layer 6, the annular member 5 provided so as to fill up a stepped space formed between a proximal portion of the resin coating layer 6 and the wire guide main body 2. Incidentally, the outside diameter of the proximal end of the resin coating layer 6 is greater than the outside diameter of the wire main body 2 at the proximal end of the resin coating layer 6, and the stepped space is formed due to the difference between these outside diameters.

Besides, the outside diameter of the distal end 52 of the annular member 5 is approximately equal to the outside diameter of the proximal end of the resin coating layer 6, and the distal end face 53 of the annular member 5 is joined to the proximal end face 61 of the resin coating layer 6. In this case, the resin coating layer 6 is so set as not to cover the annular member 5 by extending toward the proximal side beyond the distal end 52 of the annular member 5. In other words, a stepless continuous surface is formed between the distal end 52 of the annular member 5 and the proximal end of the resin coating layer 6.

In addition, the outside diameter of the annular member 5 gradually decreases from the distal side toward the proximal side (along the proximal direction), and the outside diameter of the proximal end 51 of the annular member 5 is smaller than the outside diameter of the distal end 52 of the annular member 5. Besides, the outside diameter of the proximal end 51 of the annular member 5 is approximately equal to the outside diameter of the wire main body 2 (a coating layer 7) at the proximal end 51 of the annular member 5. In other words, a stepless continuous surface is formed between the wire main body 2 (coating layer 7) and the proximal end 51 of the annular member 5. The outside diameter of the proximal end 51 of the annular member 5 is smaller than the outside diameter of the main body portion 32 of the core wire 3. The annular member 5 has a length of 0.5 to 15 mm.

In addition, the inside diameter of the proximal end 51 of the annular member 5 is greater than the inside diameter of the distal end 52 of the annular member 5. This is due to the fact that the annular member 5 is located on the tapered portion 34 of the core wire 3, as will be described later. Incidentally, the inside diameter of the proximal end 51 may be equal to the inside diameter of the distal end 52.

By the annular member 5, it is possible to prevent a proximal portion of the resin coating layer 6 from being caught on the distal end of a catheter or a medical instrument such as a riser base of an endoscope which is used in combination of the guide wire 1. Consequently, the resin coating layer 6 can be prevented from being peeled. In addition, slidability of the guide wire 1 can be prevented from being lowered due to the above-mentioned step.

Besides, the inclination angle θ (taper angle) of the annular member 5, in the present embodiment, is constant along the longitudinal direction of the core wire 3 (wire main body 2). Incidentally, the inclination angle θ may vary along the longitudinal direction at some part(s). The inclination angle θ is preferably not less than 30°, more preferably about 2 to 25°, and further preferably about 5 to 20°. This ensures that the annular member 5 can be prevented from being caught on the distal end of a catheter or a medical instrument such as a riser base of an endoscope which is used in combination with the guide wire 1.

In addition, the hardness of the annular member 5 is preferably set to be higher than the hardness of the resin coating layer 6. This ensures that the annular member 5 can be prevented from being caught on the distal end of a catheter or a medical instrument such as a riser base of an endoscope which is used in combination with the guide wire 1.

Besides, either one or both of the distal end face 53 and the inner peripheral surfaces of the annular member 5 may have been roughened. Where the distal end face 53 of the annular member 5 is roughened, adhesion thereof with the resin coating layer 6 is enhanced. Where the inner peripheral surface is roughened, adhesion thereof with a fixing material 9 to be described later is enhanced.

In addition, examples of the material which can be used to constitute the annular member 5 include various resin materials and various metallic materials. For example, the same material as that constituting the resin coating layer 6 can be used. Also, materials different from the material constituting the resin coating layer 6 can be used.

It is to be noted that the annular member 5 is preferably formed of a metallic material (metal) or a hard resin material (resin), particularly a metallic material. Examples of the material which can be used to form the annular member 5 include stainless steel, titanium, titanium alloy, Ni—Ti alloy, aluminum, gold, and platinum. When the annular member 5 is formed of a noble metal such as gold, platinum, etc. or an alloy thereof, radiopacity is enhanced. Besides, in the case of forming the annular member 5 from a metallic material, the outer periphery of the annular member 5 may be covered with a coating layer which is not shown. Examples of the material which can be used to constitute the coating layer include various resin materials, various ceramics, and various metallic materials, and, particularly, an insulating material is preferably used. In addition, in the case of forming the annular member 5 from a hard resin material, examples of the material which can be used include polycarbonate, polyamides (nylon), polyethylene terephthalate, polyacetal, and polyphenylyene sulfide.

Besides, the annular member 5 is fixed (attached) to the core wire 3 (wire main body 2) by the fixing material 9 provided on the outer periphery of the core wire 3 (wire main body 2).

The fixing material 9 is preferably composed of an adhesive, particularly an insulating adhesive. This makes it possible to insulate the core wire 3 and the annular member 5 from each other. Consequently, in the case where, for example, a medical instrument to be used by passing an electric current is disposed along the guide wire 1, leakage of current from the outer surface of the annular member 5 and the like trouble can be prevented from occurring.

Incidentally, the fixing material 9 is not limited to an adhesive. For example, in the case where the annular member 5 is formed of a metallic material, the fixing material 9 may be solder (brazing material) or the like. Also, it is natural that the method for fixing the annular member 5 is not limited to the method based on the use of a fixing material.

In addition, the annular member 5 is located at the tapered portion 34 of the core wire 3 (wire main body 2). While the whole part of the annular member 5 is located at the tapered portion 34 in the configuration shown, this is not limitative; namely, a configuration may be adopted in which only a part of the annular member 5 is located at the tapered portion 34.

The annular member 5 has a function of moderating the difference in rigidity (flexural rigidity, torsional rigidity) between the proximal side and the distal side, relative to the annular member 5, of the wire main body 2. Specifically, as above-mentioned, in the tapered portion 34 of the core wire 3, the outside diameter gradually decreases along the distal direction, and the rigidity is lowered along the distal direction. On the other hand, the wire main body 2 is provided thereon with the resin coating layer 6 on the distal side of the annular member 5. Therefore, in the case where the annular member 5 is not provided, the rigidity increases abruptly, and the possibility of kinking (sharp bending) is therefore high, at the proximal end of the resin coating layer 6. In the present guide wire 1, however, due to the presence of the annular member 5, an abrupt increase in rigidity at the proximal end of the resin coating layer 6 is prevented, and kinking at the proximal end of the resin coating layer 6 can be prevented.

Meanwhile, in the present invention, the guide wire 1 is applicable not only to guide wires to be used under radioscopy but also to guide wires to be used through an endoscope, specifically, a guide wire to be used to guide a catheter inserted in the lumen of the endoscope to a target site in a body lumen or the like (hereinafter the last-mentioned guide wire will be referred to as "transendoscopic guide wire"). Now, in the present embodiments, the cases of application of the guide wire 1 to a transendoscopic guide wire will be described representatively.

The guide wire 1 as a transendoscopic guide wire is provided with the coating layer 7 covering (coating) the outer periphery of the core wire 3, as above-mentioned (see FIGS. 1, 2 and 4). As shown in FIG. 1, the coating layer 7 covers the outer periphery of that portion of the core wire 3 which ranges from an intermediate portion (the distal portion covered with the resin coating layer 6) to a proximal-side portion of the tapered portion 34. As shown in FIGS. 2 and 4, the coating layer 7 has a first layer (ground layer) 73 and a second layer (intermediate layer) 74 and a third layer (outer layer) 75, these layers being stacked in this order from the core wire 3 side.

Incidentally, examples of the method for forming such a coating layer 7 include a method in which application and drying of a liquid material obtained by liquidizing a material for forming each layer are sequentially repeated. Besides, examples of applying the liquid material include a spraying method and a dipping method.

The first layer 73 is formed on the outer periphery of the core wire 3. The first layer 73 is formed of a material which contains a low-friction resin material capable of reducing friction and a pigment.

The low-friction resin material in the first layer 73 is preferably a fluoro-resin material, for example. Examples of the fluoro-resin material include polytetrafluoroethylene (PTFE), fluorinated ethylene propylene (FEP), tetrafluoroethylene-perfluoroalkyl vinyl ether copolymer (PFA), polychlorotrifluoroethylene (PCTFE), polyvinylidene fluoride (PVDF), polyvinyl fluoride (PVF), and tetrafluoroethylene-ethylene copolymer (PETFE). Besides, the first layer 73 may contain two kinds of fluoro-resin materials differing in composition. In this case, of the two kinds of fluoro-resin materials, for example, one may be polytetrafluoroethylene (PTFE) and the other may be fluorinated ethylene propylene (FEP).

The pigment (first pigment) in the first layer 73 may be either an inorganic pigment or an organic pigment; however, an inorganic pigment is preferred, from the viewpoint of heat resistance during formation of the first layer 73. Examples of the inorganic pigment which can be used here include carbon black, mica, titanium dioxide, nickel titanium yellow, Prussian blue, Milori blue, cobalt blue, ultramarine, and viridian. Incidentally, one pigment may be used singly, or two or more pigments may be used together (particularly, as a mixture). Besides, the average particle diameter of the pigment is, for example, preferably 0.05 to 5 µm, and more preferably 0.1 to 1.0 µm. In addition, the content of the pigment in the first layer 73 is, for example, preferably about 20 to 50 wt %, more preferably about 30 to 40 wt %, based on the whole part of the first layer 73, though depending on the kind and properties of the pigment and on the composition and properties of the resin material.

Further, since the first layer 73 is formed on the outer periphery of the core wire 3, a binder resin material functioning as a binder is contained in the material constituting the first layer 73, for the purpose of enhancing adhesion of the first layer 73 with the core wire 3. Examples of the binder resin material include polysulfone, polyimides, polyetherether ketone, polyarylene ketone, polyphenylene sulfide, polyarylene sulfide, polyamide-imides, polyether imides, polyimide sulfone, polyaryl sulfone, polyaryl ether sulfone, polyesters, polyether sulfone, and epoxy resin.

As shown in FIG. 2, the first layer 73 configured as above has a constant thickness along the wire longitudinal direction, and its average thickness t1 is the smallest of the average thicknesses of the first layer 73, the second layer 74 and the third layer 75. With the first layer 73 being the thinnest layer, the overall thickness of the coating layer 7 can be reduced to such an extent that the second layer 74 can be clearly confirmed visually, as will be described later. In addition, the reduction in the overall thickness of the coating layer 7 promises flexibility of the guide wire 1 assuredly. Besides, there is a merit that a reduction in sliding resistance can also be secured due to the reduction in radial size.

Incidentally, the average thickness t1 is, for example, preferably 0.002 to 0.015 mm, more preferably 0.004 to 0.008 mm.

As shown in FIGS. 2 and 4, the second layer 74 is formed on the first layer 73 in such a manner as to cover the first layer 73. The second layer 74 is formed of a material composed only of a low-friction resin material and a pigment, that is, formed of a material obtained by omitting the binder resin material from the material constituting the first layer 73.

As the low-friction resin material in the second layer 74, there can be used, for example, such low-friction resin materials as mentioned in the description of the first layer 73 above. In this case, the low-friction resin material in the second layer 74 and the low-friction resin material in the first layer 73 may be the same or different.

The pigment (second pigment) in the second layer 74 may be either an inorganic pigment or an organic pigment; however, an inorganic pigment is preferred, from the viewpoint of heat resistance during formation of the second layer 74. As the inorganic pigment, there can be used the same ones as mentioned in the description of the first layer 73 above. In addition, the content of the pigment in the second layer 74 is, for example, preferably about 10 to 50 wt %, more preferably about 20 to 30 wt %, based on the whole part of the second layer 74, though depending on the kind and properties of the pigment and on the composition and properties of the resin material.

Besides, the color of the pigment in the second layer 74 and the color of the pigment in the first layer 73 are different from each other. Further, the color of the pigment in the first layer 73 is preferably deeper than the color of the pigment in the second layer 74. In this case, for example, a configuration may be adopted in which the pigment in the first layer 73 is carbon black whereas the pigment in the second layer 74 is nickel titanium yellow. In addition, while such a combination of the pigments contained respectively in the layers can be adopted, the pigments may be appropriately selected in such a manner that the colors of the pigments contained respectively in the layers are complementary to each other. In the case where the colors are complementary, a combination may be adopted in which the pigment in the first layer 73 is carbon black which is black in color, whereas the pigment in the second layer 74 is titanium dioxide which is white in color. Or, on the contrary, a combination may be adopted in which the pigment in the first layer 73 is titanium dioxide which is white, whereas the pigment in the second layer 74 is carbon black which is black.

Besides, where the first layer 73 is colorless and transparent, the light transmitted through the second layer 74 and the third layer 75 is incident on and reflected by the core wire 3, so that the second layer 74 is seen in a see-through manner. The brighter the color of the second layer 74, the more conspicuously the second layer 74 is seen in a see-through manner. In addition, since the binder resin in the first layer 73 is mostly transparent brown, the color is rather brown and similar to the color of the second layer 74 than the reflected light from the core wire 3, and cannot be said to be a clear color. In order to obviate such a problem, the first layer 73 is preferably provided with a color which inhibits transmission of light therethrough; therefore, the content of the pigment in the first layer 73 is significant.

In the guide wire 1, on the basis of structure of the coating layer 7, the first layer 73 is a "ground" for (is functioning as a "ground" for) the second layer 74. Therefore, where the pigment in the first layer 73 and the pigment in the second layer 74 are selected as above-mentioned, the second layer 74 will be comparatively high in brightness and saturation, so that the second layer 74 can be clearly confirmed visually when the guide wire 1 is observed from outside a living body through an endoscope. Consequently, the position of the distal-side portion (the portion protruding from the distal end of the lumen of the endoscope) of the guide wire 1 in a living body can be grasped easily and assuredly. Thus, it can be said that the coating layer 7 in the guide wire 1 has a function of indicating the position of the guide wire 1 (wire main body 2) in a living body.

In addition, as above-mentioned, the material constituting the second layer 74 is a material in which a binder resin is omitted. This ensures that, during drying of a liquid material obtained by liquidizing the material for forming the second layer 74, discoloration of a binder resin material due to the heat for drying is prevented securely. Consequently, the color of the second layer 74 itself (whole part) can be made to be the color of the pigment in the second layer 74. Accordingly, the second layer 74 is clearly confirmed visually.

As shown in FIG. 2, the second layer 74 thus configured has a thickness which is constant along the wire longitudinal direction, and the average thickness t2 thereof is greater than the average thickness t1 and the average thickness t3 of the third layer 75; in other words, the average thickness t2 is the largest. This ensures that the second layer 74 is particularly emphasized in the coating layer 7, so that the second layer 74 can be visually confirmed more clearly. Besides, where carbon black is contained in the second layer 74, the carbon black exhibits not only an effect on shade but also an effect as filler, leading to an enhanced film strength. Since the layer with these effects exhibited is the thickest of the layers, it is advantageous for enhancing the film strength of the coating layer 7.

Incidentally, the average thickness t2 is, for example, preferably 0.002 to 0.020 mm, more preferably 0.005 to 0.015 mm. In addition, while the average thickness t2 is greater than the average thickness t3 in the configuration shown in FIG. 2, this is not limitative; specifically, the average thickness t2 is substantially the same as the average thickness t3.

Thus, in the guide wire 1, the thicknesses of the layers constituting the coating layer 7 can respectively be set appropriately. This makes it possible to prevent the coating layer 7 from becoming excessively thick. Accordingly, flexibility of the guide wire 1 (the distal-side portion) can be secured assuredly.

As shown in FIGS. 2 and 4, the third layer 75 is formed on the second layer 74 in such a manner as to cover the second layer 74. The third layer 75 has such a degree of transparency as to permit the second layer 74 and the marker 12 to be visually confirmed.

The third layer 75 can be formed for various purposes. One example of the purposes is to reduce friction (sliding resistance) on the guide wire 1 and to enhance slidability, thereby enhancing operability of the guide wire 1.

In order to contrive a reduction in friction (sliding resistance) on the guide wire 1, the third layer 75 is formed of a low-friction resin material such as those mentioned in description of the first layer 73 above. As a result, the frictional resistance (sliding resistance) between the guide wire 1 and the inside wall defining the lumen of an endoscope (or a catheter, as well) used together with the guide wire 1 is reduced, whereby slidability is enhanced, and operability of the guide wire 1 inside the endoscope is more improved. In addition, with the sliding resistance of the guide wire 1 thus reduced, it is possible to more securely prevent the guide wire 1 from kinking (sharp bending) or torsion when the guide wire 1 is moved and/or rotated inside the endoscope.

Besides, the low-friction resin material constituting the third layer 7 has an insulating property. Since a distal portion of the third layer 75 enters into the inside of the annular member 5 and the annular member 5 is located on the outer periphery of the third layer 75, the insulating property possessed by the third layer 75 enables insulation between the core wire 3 and the annular member 5. This ensures that leakage of current from the outer surface of the annular member 5 and the like trouble can be prevented from occurring in the case where a medical instrument to be used by passing an electric current is disposed along the guide wire 1.

The average thickness t3 of the third layer 75 is, for example, preferably 0.002 to 0.020 mm, more preferably 0.005 to 0.015 mm. The average thickness t3 of the third layer 75 is preferably as small as the average thickness t2 of the second layer 74. In the case where the outside diameter of the guide wire 1 is prescribed, if the average thickness t2 of the second layer 74 is set large for enhancing the film strength of the coating layer 7, the average thickness t3 of the third layer 75 must be set small. In this case, if the average thickness t3 of the third layer 75 is attempted too small, a problem arises in that, at the time when gaps (the rhombic areas surrounded by a first linear portion 121 and a second linear portion 122 in FIG. 1) in the protuberant marker 12 are coated with the third layer 75, the material of the third layer 75 would be repelled, without being deposited favorably, so that uneven coating results. Therefore, it is preferable for the third layer 75 to have such a thickness that the material of the third layer 75 can be deposited on the gaps in an assured manner.

As shown in FIGS. 2 and 4, the marker 12 is disposed between the second layer 74 and the third layer 75 of the coating layer 7. The marker 12 has a function of indicating the position of the guide wire 1 (wire main body 2) in a living body.

As shown in FIGS. 1, 5 and 6, the marker 12 is composed of the first linear portion 121 and the second linear portion 122.

The first linear portion 121 is wound spirally. This ensures that the first linear portion 121 is provided over the whole periphery of the wire main body 2. In addition, the first linear portion 121 is sparsely wound so that the adjacent line portions thereof are spaced from each other.

The second linear portion 122 is spirally wound like the first linear portion 121, but the winding direction thereof is opposite to the winding direction of the spiral of the first linear portion 121. This ensures that the second linear portion 122 is provided over the whole periphery of the wire main body 2. In addition, like the first linear portion 121, the second linear portion 122 is sparsely wound so that the adjacent line portions thereof are spaced from each other.

With the first linear portion 121 and the second linear portion 122 formed in this manner, they intersect each other at a plurality of positions, so that the marker 12 as a whole is grid-like in shape.

Incidentally, as shown in FIG. 2, the first linear portion 121 and the second linear portion 122 are substantially rectangular in shape in longitudinal section, with the top portion of the substantially rectangular shape being curved in a protuberant shape. In addition, the height of the first linear portion 121 and the second linear portion 122 is, for example, preferably 3 to 8 μm, more preferably 3 to 5 μm.

The first linear portion 121 and the second linear portion 122 are each formed of a material containing a resin material and a pigment. The material constituting the first linear portion 121 and the material constituting the second linear portion 122 are substantially the same. In view of this, the material constituting the first linear portion 121 will be described representatively.

The color of the first linear portion 121 is determined mainly by the kind and properties of the pigment contained in the first linear portion 121, the composition and properties (particularly, tone and the like) of the resin material, and the content of the pigment, and can be freely set by regulating these factors.

Here, in order to recognize the movement of the guide wire 1 through an endoscope, the color of the first linear portion 121 is one of important factors, like the color of the second layer 74. Therefore, the combination of the color of the first linear portion 121 with the color of the second layer 74 serving as a ground for the first linear portion 121 should be taken into consideration.

As an example, a case may be considered in which the second layer 74 is silver white (metallic color), and the first linear portion 121 has a red or yellow color, which is different from the color of the second layer 74. In this case, the difference in brightness between the two colors is large (high contrast), which promises high visibility of the first linear portion 121 and is therefore preferable. Also, in the case where the two colors are complementary to each other, the visibility of the first linear portion 121 is also high, which is preferable. In addition, selection of a combination of colors capable of exhibiting a clear contrast, such as a color of yellow, yellowish green, orange or the like against black or a deep color (charcoal gray, dark brown, deep blue, purple, or the like), and a color of red, orange, pink or the like against blue, is particularly preferable. Besides, a combination of analogous colors different in shade, such as a combination of dark blue with light blue, a combination of reddish-brown with pink, etc. may also be used.

The resin material contained in the material constituting the first linear portion 121 is, for example, preferably the following (1) or (2).

(1) As the resin material contained in the material constituting the first linear portion 121, there is preferably used a resin material (heat-resistant resin material) having a melting point of not less than 200° C., more preferably a resin material having a melting point of about 2000 to 300° C.

Examples of the resin material having a melting point of not less than 200° C. include polysulfone, polyimides, polyether-ether ketone, polyarylene ketone, polyphenylene sulfide, polyarylene sulfide, polyamide-imides, polyether imides, polyimide sulfone, polyaryl sulfone, polyaryl ether sulfone, polyesters, polyether sulfone, and fluoro-resins such as polytetrafluoroethylene (PTFE), ethylene-tetrafluoroethylene copolymer (ETFE), etc., of which one may be used or two or more may be used in combination.

(2) As the resin material contained in the material constituting the first linear portion 121, there is preferably used a thermosetting resin material.

Examples of the thermosetting resin material include epoxy resin, phenolic resin, polyesters (unsaturated polyesters), polyimides, silicone resin, and polyurethane, of which one may be used or two or more may be used in combination.

In addition, in order to obtain a good color, the content of the pigment in the first linear portion 121 is preferably about 10 to 90 wt %, more preferably 20 to 50 wt %, based on the whole part of the first linear portion 121, though depending on the kind and properties of the pigment and the composition and properties of the resin material.

While the pigment in the first linear portion 121 is preferably dispersed uniformly, the pigment may be present in an unevenly distributed manner, for example, on the outer surface side of the first linear portion 121. The pigment may be either an inorganic pigment or an organic pigment; however, an inorganic pigment is preferred, from the viewpoint of heat resistance. As the inorganic pigment, there can be used the same ones as mentioned in the description of the first layer 73 above.

The marker 12 as above can be formed, for example, in the manner as follows.

Of the first linear portion 121 and the second linear portion 122, the first linear portion 121 is formed in precedence to the second linear portion 122.

In forming the first linear portion 121, first, a masking tape is spirally wound around and adhered to that portion of the second layer 74 formed on the core wire 3 to be the wire main body 2 which is exclusive of the region where the first linear portion 121 is to be formed.

Next, that exposed portion of the second layer 74 on which the masking tape is not wound is coated with a liquid matter of the material for forming the first linear portion 121. Example of the coating method here include a spraying method and a dipping method.

Subsequently, the liquid material thus applied is dried. Thereafter, the masking tape is peeled off (removed).

By such a process, the first linear portion 121 can be formed. Next, the second linear portion 122 is formed.

In forming the second linear portion 122, first, a masking tape is spirally wound (in the direction opposite to the above-mentioned) around and adhered to that portion of the second layer 74 formed thereon with the first linear portions 121 which is exclusive of the region where the second linear portion 122 is to be formed.

Next, like in the formation of the first linear portions, that exposed portion of the second layer 74 on which the masking tape is not wound is coated with the liquid material.

Subsequently, the liquid material thus applied is dried. Thereafter, the masking tape is peeled off (removed).

By such a process, the second linear portion 122 partly overlapping on the first linear portions 121 can be formed. In addition, at intersection portions 123 between the first linear portion 121 and the second linear portion 122, the intersection portions 123 are raised in the radial direction of the core wire 3 (wire main body 2).

Incidentally, only one first linear portion 121 and only one second linear portion 122 may be formed, or a plurality of first linear portions 121 and a plurality of second linear portions 122 may be formed. Besides, the number of the first linear portion(s) 121 formed and the number of the second linear portion(s) 122 formed may be the same or different.

In addition, while the first linear portion 121 and the second linear portion 122 have the same width in the configuration shown in FIG. 1, this is not limitative; namely, they may have different widths.

The marker 12 configured as above is observed in the state as shown in FIGS. 5 and 6, when the guide wire 1 is observed from outside a living body through an endoscope. Referring to FIG. 5, a case where the guide wire 1 is rotated about the axis thereof will be described, and, referring to FIG. 6, a case where the guide wire 1 is moved along the axial direction thereof will be described.

First, the case where the guide wire 1 is rotated about its axis will be described.

FIG. 5(a) illustrates the condition before the guide wire 1 is rotated. Then, the guide wire 1 is rotated by a predetermined amount (angle) in the direction of arrow in the figure, whereon the condition illustrated in FIG. 5(b) is obtained.

As above-mentioned, the marker 12 is provided with a plurality of intersection portions (points of intersection) 123 where the first linear portion 121 and the second linear portion 122 intersect each other (see FIG. 1). Here, paying attention to the intersection portions 123a, 123b, 123c, 123d, 123e and 123f between the first linear portion 121 and the second linear portion 122 which can be actually observed (in FIG. 5(a)), these intersection portions 123a to 123f in FIG. 5(b) appear to have been moved to the lower side in the figure, as compared to the condition shown in FIG. 5(a).

Since the marker 12 can be visually checked in this manner, when the guide wire 1 has been rotated about its axis by exerting a torque on the guide wire 1, it is possible to securely confirm (grasp) that "the guide wire 1 has been rotated."

In addition, when the guide wire 1 is rotated in the direction opposite to the above-mentioned, the intersection portions 123a to 123f are moved from the condition of FIG. 5(a) toward the upper side in the figure. This makes it possible to check also in which direction the guide wire 1 is being rotated, that is, the rotating direction of the guide wire 1.

Now, a case where the guide wire 1 is moved along the axial direction thereof will be described below.

FIG. 6(a) illustrates a condition before the guide wire 1 is moved. When the guide wire 1 is moved by a predetermined amount (distance) in the direction of arrow, the condition shown in FIG. 6(b) is obtained.

Here, paying attention to the intersection portions 123a to 123f between the first linear portion 121 and the second linear portion 122 which can be actually observed (in FIG. 6(a)), these intersection portions 123a to 123f in FIG. 6(b) appear to have been moved along the distal direction (leftward in the figure), as compared with the condition of FIG. 6(a). In addition, the intersection portions 123a and 123b come out of (disappear from) the visual field (visual field region).

Since the marker 12 can thus visually confirmed, upon movement of the guide wire 1 along the axial direction thereof by pushing the guide wire 1 in the distal direction, it is possible to securely confirm (grasp) that "the guide wire 1 has been moved."

Besides, when the guide wire 1 is moved in the direction opposite to the above-mentioned by pulling it, the intersection portions 123a to 123f are moved in the proximal direction (rightward in the figure), as compared with the condition of FIG. 6(a). This makes it possible to check also in which direction the guide wire 1 is being moved, that is, the moving direction of the guide wire 1.

As above-mentioned, in the guide wire 1, it is ensured that, when the guide wire 1 is moved along its axis or rotated about its axis, it is possible to securely discriminate, by the above-mentioned change of the marker 12, whether the actual displacement of the guide wire 1 is movement or rotation.

In addition, in the case of a guide wire provided with a single spiral marker as that in the prior art, even upon rotation of the guide wire about its axis by exerting a torque on the guide wire, the operator would gets an illusion as if the guide wire had been advanced or retracted (moved), contrary to the operator's thought to have rotated the guide wire. In the case of the present guide wire 1, however, such an illusion can be securely prevented, and operability is excellent.

As shown in FIG. 1, at the same position in the axial direction of the wire main body 2, specifically at the main body portion 32 and the tapered portion 34 of the wire main body 2, the spiral pitch of the first linear portion 121 and the spiral pitch of the second linear portion 122 are the same in magnitude. This ensures that a plurality of intersection portions 123 are favorably dispersed in the region where the marker 12 is formed, and, therefore, the visual confirmability of each of the intersection portions 123 is enhanced. Besides, there is also a merit that rotation of the guide wire 1 and pushing-in/out of the guide wire 1 can be easily discriminated from each other.

In addition, the marker 12 is provided with a decreasing pitch portion 124 where the respective spiral pitches of the first linear portion 121 and the second linear portion 122 are gradually decreasing along the distal direction in the tapered portion 34. By confirming the decreasing pitch portion 124, it is possible to grasp that the wire main body 2 is reduced in radial size and high in flexibility at the portion under consideration.

As shown in FIG. 1 (and in FIGS. 5 and 6, also), the width of the first linear portion 121 and the width of the second linear portion 122 are the same. This makes it possible, in forming the marker 12, to omit a step of changing the linear portion width according to each of the linear portions. Accordingly, the marker 12 can be formed easily.

Incidentally, the width of the first linear portion 121 and the second linear portion 122 is preferably 0.5 to 2 times, more preferably 0.5 to 1.5 times, the average diameter of the wire main body 2. If the linear portion width exceeds the upper limit of such a numerical value range, halation may be generated, depending on the intensity of light radiated from an endoscope, at the time when the marker 12 is visually checked.

Besides, the first linear portion 121 and the second linear portion 122 may be the same or different in color; particularly, they are preferably different in color. In the case where the first linear portion 121 and the second linear portion 122 are different in color, if the first linear portion 121 and the second linear portion 122 are visually checked as if they were separating from each other, upon rotation of the guide wire 1 about its axis, the rotation is distinguished as rotation in the direction of arrow in FIG. 5. On the contrary, if the first linear portion 121 and the second linear portion 122 are visually checked as if they were approaching each other, the rotation of the guide wire 1 is distinguished as rotation in the reverse direction to the above, namely, in the direction opposite to the direction of arrow in FIG. 5.

Thus, in the guide wire 1, the marker 12 and the coating layer 7 each have the function of indicating the position of the guide wire 1 in a living body, and, therefore, one of them can be said to as "a first marker" and the other can be said to be "a second marker."

As shown in FIG. 3, in the marker 12, the height of the intersection portions 123 is greater than the height of the other portions, namely, those portions of the first linear portion 121 and the second linear portion 122 which are exclusive of the intersection portions 123. Incidentally, the height of the intersection portions 123 is, for example, preferably 3 to 10 μm, more preferably 5 to 8 μm.

As above-mentioned, the marker 12 is covered with the third layer 75. The third layer 75, at its outer surface (the outer surface of the guide wire 1) has a structure in which the parts where the intersection portions 123 of the marker 12 are disposed are raised in relation to the parts where the intersection portions 123 of the marker 12 are not disposed. In other words, raised portions (protuberant portions) 71 are formed at the parts where the intersection portions are disposed, while hollowed portions (recessed portions) 72 are formed at the parts where the intersection portions 123 of the marker 12 are not disposed. This arises from the fact that, since the third layer 75 is comparatively thin, the outer surface of the third layer 75 are, under the influence of the intersection portions 123, raised according to (shaped according to) the shape and pattern of the intersection portions 123.

As a result, the area of contact between the outer surface of the third layer 75 and the inside wall defining the lumen of the endoscope is reduced, whereby frictional resistance (sliding resistance) is reduced, slidability is enhanced, and operability of the guide wire 1 is improved.

In addition, the raised portions 71 and the hollowed portions 72 are not formed by direct processing of the third layer 72 but formed under the influence of the intersection portions 123 beneath the third layer 75. Therefore, no pointed angular part, crest or the like is formed in the outer surface of the third layer 75, and the outer surface is smooth. In other words, the raised portions 71 are rounded according to and similarly to the roundness of the top parts of the first linear portion 121 and the second linear portion 122. This promises further enhancement of slidability and very high safety.

Besides, at least the outer surface of a distal portion of the guide wire 1 is preferably coated with a hydrophilic material. This ensures that the hydrophilic material produces lubricity through wetting, whereby friction (sliding resistance) on the guide wire 1 is reduced, and slidability is further enhanced. Accordingly, operability of the guide wire 1 is further enhanced.

Examples of the hydrophilic material include cellulose polymers, polyethylene oxide polymers, maleic anhydride polymers (e.g., maleic anhydride copolymer such as methyl vinyl ether-maleic anhydride copolymer), acrylamide polymers (e.g., polyacrylamide, polyglycidyl methacrylate-dimethylacrylamide (PGMA-DMAA) block copolymer), water-soluble nylons, polyvinyl alcohol, and polyvinyl pyrrolidone.

Such a hydrophilic material, in many cases, exhits lubricity through wetting (water absorption), to thereby reduce the frictional resistance (sliding resistance) between the guide wire 1 and the inside wall of a catheter or an endoscope used together with the guide wire 1. As a result, slidability of the guide wire 1 is further enhanced, and operability of the guide wire 1 inside the catheter is further improved.

<Second Embodiment>

Figure 7:
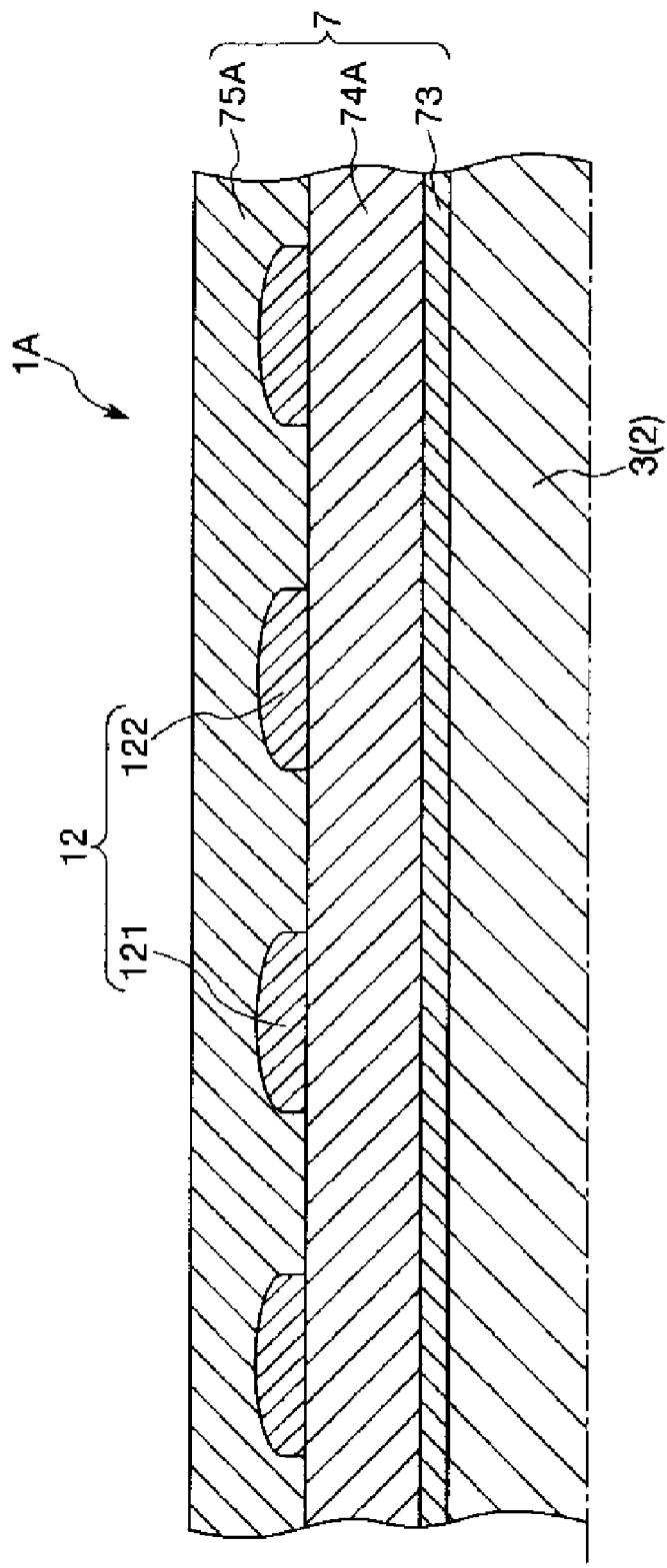
FIG. 7 is a longitudinal sectional view showing an embodiment (second embodiment) in the case where the medical instrument of the present invention is applied to a guide wire.

FIG. 7 is a longitudinal sectional view showing an embodiment (second embodiment) in the case where the medical instrument of the present invention is applied to a guide wire.

Now, referring to this figure, a second embodiment of the medical instrument according to the present invention will be described below. The following description will be centered on differences from the above-described embodiment, and descriptions of the same items as above will be omitted.

This embodiment is the same as the above-described first embodiment, except for difference as to the material constituting the second layer.

The material constituting a second layer 74A of a guide wire 1A shown in FIG. 7 further contains a binder resin material, in addition to a low-friction resin material and a pigment. The content of the binder resin material in the second layer 74A is lower than the content of a binder resin material in a first layer 73.

Such a configuration ensures that, during drying of a liquid material obtained through liquidizing the material for constituting the second layer 74A in forming the second layer 74A, the binder resin material is securely restrained from being discolored to yellow, liver brown or the like color due to the heat for drying. As a result, the color of the second layer 74A itself (whole part) becomes a color in which the color of the pigment in the second layer 74A appears with priority, namely, a color composed mainly of the color of the pigment in the second layer 74; therefore, the second layer 74 is clearly confirmed visually. This ensures that, when the guide wire 1 is observed from outside a living body through an endoscope, the position of a distal-side portion (a portion protruding from the distal end of the lumen of the endoscope) of the guide wire 1 in the living body can be grasped easily and assuredly.

Incidentally, the content of the binder resin material in the second layer 74A is, for example, preferably 0 to 0.5 times, more preferably 0 to 0.2 times, the content of the binder resin material in the first layer 73. This ensures that the above-mentioned discoloration of the binder resin material in the second layer 74A is restrained more assuredly.

In addition, as the binder resin material in the second layer 74A, there can be used such materials as mentioned in the description of the first layer 73 of the guide wire 1 in the first embodiment above. In this case, the binder resin material in the second layer 74A may be of the same kind as or different kind from the binder resin material in the first layer 73.

As shown in FIG. 7, the third layer 75A has a thickness which is sufficiently secured so that the third layer 75A is not influenced by the raising of (ruggedness relevant to) the marker 12. As a result, the third layer 75A can be made to be a layer in which raised portions 71 or hollowed portions 72 as present in the third layer 75 in the first embodiment above are not generated in the outer surface thereof, that is, in which the longitudinal sectional shape of the outer surface is rectilinear.

<Third Embodiment>

Figure 8:
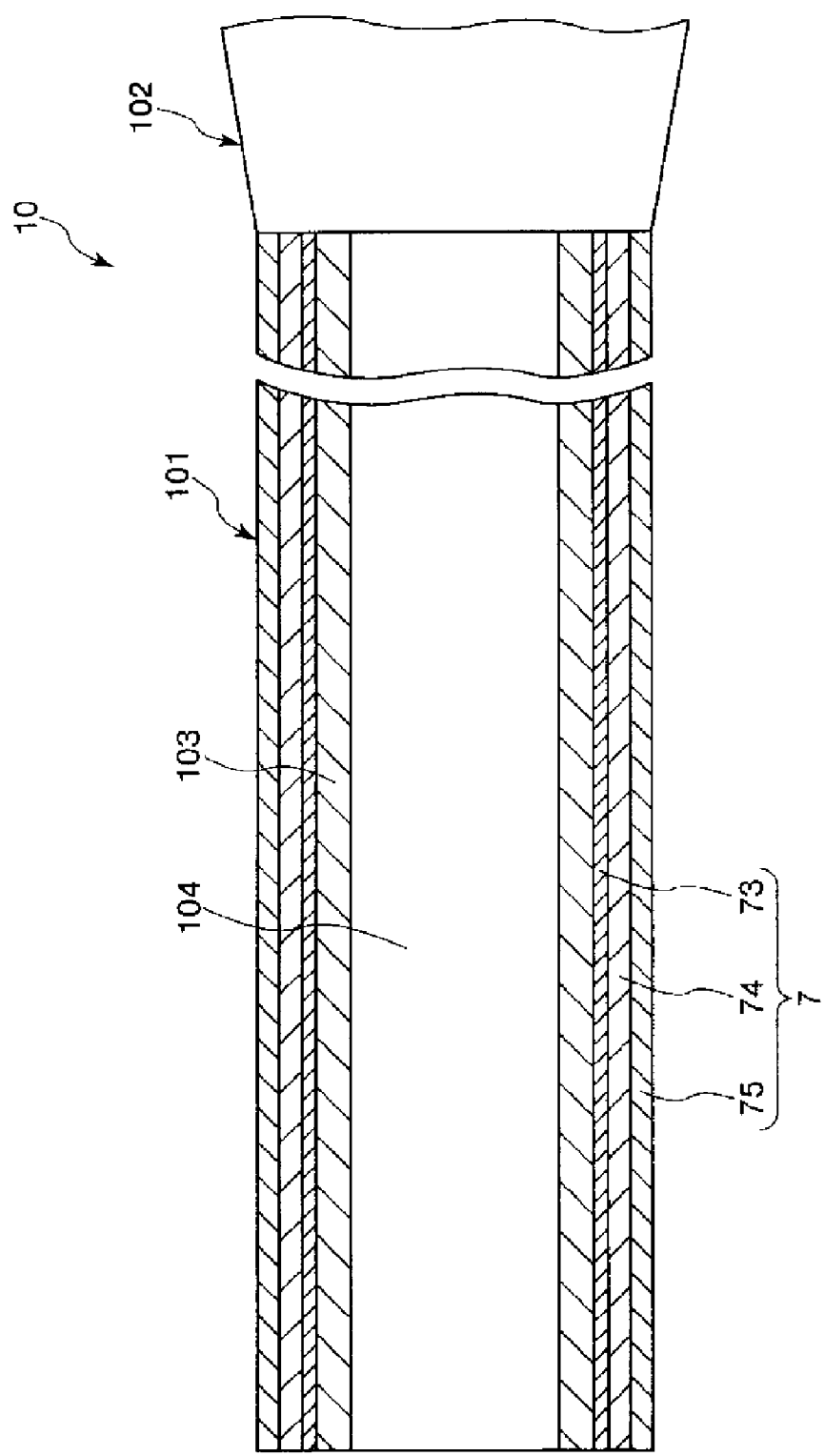
FIG. 8 is a longitudinal sectional view showing an embodiment (third embodiment) in the case where the medical instrument of the present invention is applied to a catheter.

FIG. 8 is a longitudinal sectional view of an embodiment (third embodiment) in the case where the medical instrument of the present invention is applied to a catheter.

Now, referring to this figure, a third embodiment of the medical instrument according to the present invention will be described below. The following description will be centered on differences from the above-described embodiments, and description of the same items as above will be omitted.

This embodiment is the same as the above-described first embodiment, except for difference in configuration (shape) of the medical instrument.

A catheter 10 shown in FIG. 8 has a catheter main body (medical instrument main body) 101 composed of a flexible tube, and a hub 102 fixed to a proximal portion of the catheter main body 101. The hub 102 is tubular in shape, and its inner cavity communicates with the inside of the catheter main body 101.

The catheter main body 101 is composed of an inner layer 103 as a core tube located on the inner side, and a coating layer 7 as an outer layer formed on the outer periphery of the inner layer 103. An inner peripheral surface of the inner layer 103 defines a lumen 104.

In the catheter main body 101 configured as above, like in the guide wire 1 of the first embodiment above, a second layer 74 is comparatively high in brightness and saturation. Therefore, the catheter main body 101 (a coating layer 7 (a second layer 74)) can be clearly confirmed visually. Consequently, the position of the catheter main body 101 in a living body can be grasped easily and assuredly.

Incidentally, a marker for indicating the position of the catheter main body 101 in a living body, like the marker 12 in the guide wire 1 of the first embodiment above, may be disposed in the coating layer 7.

While the medical instrument according to the present invention has been described above referring to the embodiments shown in the drawings, the invention is not limited to the embodiments, and each of the components of the medical instrument can be replaced by one with an arbitrary configuration which can exhibit the same function as that of the original component. Besides, an arbitrary structure or structures may be added.

In addition, the medical instrument according to the present invention may be a combination of arbitrary two or more configurations (features) of the above-described embodiments.

Besides, while the cases of application of the medical instrument of the present invention to a guide wire or a catheter have been described above, the medical instrument of the invention may be applied, for example, to a dilator including, as a main body, a tube similar to the catheter main body of a catheter.

In addition, while the first layer of the coating layer contains the pigment, this is not limitative, and the pigment in the first layer may be omitted.

Besides, the first linear portion and the second linear portion are not limited to those which are formed by drying a liquid material. For instance, the linear portions may each be a member obtained by spirally winding a belt-like (ribbon-like) member.

In addition, the case where a marker is disposed in the coating layer of the guide wire has been described in the first embodiment and the second embodiment above, this is not limitative, and the marker may be omitted.

Besides, while the case in which the coating layer covers at least the outer periphery of a distal-side portion of the linear body (wire main body, or catheter main body) has been described above, the coating layer may cover a part of the linear body or the whole part of the linear body.

INDUSTRIAL APPLICABILITY

The medical instrument according to the present invention is a medical instrument to be inserted into a living body when being used, including: a medical instrument main body which includes a long linear body having flexibility and on which a coating layer covering at least the outer periphery on the distal side thereof is formed, wherein the coating layer includes: a first layer which includes a material containing a low-friction resin material capable of reducing friction and a binder resin material functioning as a binder; a second layer which is formed on the first layer and includes a material containing the low-friction resin material and a pigment and in which the content of the binder resin material is lower than the binder resin material content of the first layer or nil; and a third layer which is formed on the second layer and includes a material containing the low-friction resin material. Therefore, flexibility of a distal-side portion of the medical instrument can be secured assuredly, and the position of that portion in a living body can be grasped easily and assuredly. Accordingly, the medical instrument of the present invention has industrial applicability.

The invention claimed is:

1. A medical instrument to be inserted into a living body when being used, comprising:
a medical instrument main body which includes a long linear body having an outer periphery and providing flexibility, a coating layer covering at least the outer periphery of the long linear body, the coating layer being formed on at least a distal side of the long linear body, wherein the coating layer includes:
a first layer which includes a material containing a low-friction resin material capable of reducing friction and a binder resin material functioning as a binder, the entire first layer being directly in contact with the medical instrument main body;
a second layer which is formed on the first layer and includes a material containing the low-friction resin material and a pigment and in which the content of the binder resin material is lower than the binder resin material content of the first layer or nil;
a marker disposed on the second layer, wherein the marker has a plurality of linear portions having a color which is different from a color of the second layer so as to enable endoscopic viewing of the marker by a user when the medical instrument is internally disposed within the living body, said plurality of linear portions defining a plurality of gaps therebetween; and
a third layer which is formed on the second layer and includes a material containing the low-friction resin material;
wherein the third layer directly contacts the marker and directly contacts the second layer at the plurality of gaps between the plurality of linear portions such that the marker is thereby disposed between the second layer and the third layer.

2. The medical instrument according to claim 1, wherein said marker has a function of indicating a position of the medical instrument main body in the living body and includes a material containing a pigment different in color from the pigment in the second layer.

3. The medical instrument according to claim 2, wherein the marker includes a first linear portion and a second linear portion made to intersect each other at a plurality of positions so that the marker as a whole is grid-like in shape.

4. The medical instrument according to claim 3, wherein the marker has the first linear portion and the second linear portion raised in radial directions of the medical instrument main body; and at intersection portions where the first linear portion and the second linear portion intersect each other, one of the first linear portion and the second linear portion is laid on the other.

5. The medical instrument according to claim 4, wherein the third layer has a raised portion which is raised from an outer surface thereof.

6. The medical instrument according to claim 2, wherein the marker is wound spirally.

7. The medical instrument according to claim 1, wherein the coating layer has a function of indicating a position of the medical instrument main body in the living body.

8. The medical instrument according to claim 1, wherein the first layer is the smallest in average thickness, among the first layer, the second layer and the third layer.

9. The medical instrument according to claim 1, wherein an average thickness of the second layer is equal to or greater than an average thickness of the third layer.

10. The medical instrument according to claim 1, wherein the second layer contains the binder resin material, and the content of the binder resin material is less than 0.5 times the binder resin material content of the first layer.

11. The medical instrument according to claim 1, wherein the low-friction material is a fluoro-resin material.

12. The medical instrument according to claim 1, wherein the pigment is an inorganic pigment.

13. The medical instrument according to claim 1, wherein the first layer contains a pigment which is different in color from the pigment in the second layer.

14. The material instrument according to claim 13, wherein the color of the pigment in the first layer is deeper than the color of the pigment in the second layer.

15. The medical instrument according to claim 1, wherein the marker disposed between the second layer and the third layer is separate and distinct from the second layer and the third layer.

* * * * *